(12) United States Patent
Cotrell

(10) Patent No.: US 8,673,833 B2
(45) Date of Patent: Mar. 18, 2014

(54) LOW IRRITANCY CLEANSING COMPOSITIONS

(75) Inventor: Philip Cotrell, Salisbury, NC (US)

(73) Assignee: Innospec Limited (GB)

( * ) Notice: Subject to any disclaimer, the term of this patent is extended or adjusted under 35 U.S.C. 154(b) by 0 days.

(21) Appl. No.: 13/386,704

(22) PCT Filed: Aug. 2, 2010

(86) PCT No.: PCT/GB2010/051269
§ 371 (c)(1),
(2), (4) Date: Feb. 23, 2012

(87) PCT Pub. No.: WO2011/015857
PCT Pub. Date: Feb. 10, 2011

(65) Prior Publication Data
US 2012/0142571 A1 Jun. 7, 2012

Related U.S. Application Data

(60) Provisional application No. 61/230,868, filed on Aug. 3, 2009.

(51) Int. Cl.
*C11D 1/02* (2006.01)
*C11D 1/34* (2006.01)
*C11D 1/94* (2006.01)

(52) U.S. Cl.
USPC ........... 510/125; 510/127; 510/130; 510/136; 510/137; 510/138; 510/499; 510/501; 510/505; 510/506

(58) Field of Classification Search
USPC ......... 510/125, 127, 130, 136, 137, 138, 499, 510/501, 505, 506
See application file for complete search history.

(56) References Cited

U.S. PATENT DOCUMENTS

2008/0255014 A1 10/2008 Luu et al.

FOREIGN PATENT DOCUMENTS

| WO | 9409763 A1 | 5/1994 |
|---|---|---|
| WO | 2007130390 A2 | 11/2007 |
| WO | 2009063250 A2 | 5/2009 |
| WO | 2011007174 A2 | 1/2011 |

OTHER PUBLICATIONS

International Search Report and Written Opinion in International Application No. PCT/GB2010/051269 mailed Feb. 16, 2012.

*Primary Examiner* — Gregory Delcotto
(74) *Attorney, Agent, or Firm* — Burns & Levinson, LLP; Janine M. Susan

(57) ABSTRACT

A low irritancy cleansing composition comprises: (a) an anionic surfactant compound of formula (I): wherein $R^1$ represents a $C_{4-36}$ substituted or unsubstituted hydrocarbyl group; each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation; and (b) an amphoteric surfactant; wherein the molar ratio of component (a) to component (b) is from 0.25:1 to 4:1 and wherein the composition comprises less than 3 wt % polyethoxylated non-ionic species.

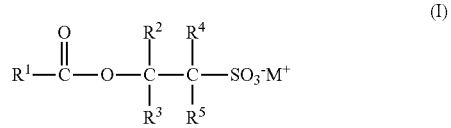

(I)

11 Claims, No Drawings

LOW IRRITANCY CLEANSING COMPOSITIONS

CROSS-REFERENCE TO RELATED APPLICATIONS

This application is a U.S. national stage application under 35 U.S.C. 371 of co-pending International Application No. PCT/GB10/51269 filed Aug. 2, 2010 and entitled "COMPOSITION", which in turn claims priority to U.S. Provisional Patent Application No. 61/230,868 filed Aug. 3, 2009, both of which are incorporated by reference herein in their entirety for all purposes.

The present invention relates to low irritancy cleansing compositions, for example compositions suitable for use as baby shampoos, baby baths, mild skin cleansers, mild facial cleansers, cleansers for sensitive skin and the like. Such compositions must exhibit low skin and eye irritation. Low irritancy cleansing compositions of this type may also be useful in animal applications, for example as pet shampoos.

Traditional shampoo formulations often contain polyoxyethylene-alkyl sulphate type anionic surfactants as a major ingredient. However these compounds have been found to cause eye and skin irritation thus limiting their use in products where low irritation is essential, for example in baby shampoos.

Various compositions of the prior art have been prepared to try to provide shampoo formulations having reduced irritancy. These typically comprise combinations of anionic and amphoteric surfactants along with significant levels of non-ionic surfactants.

For example, U.S. Pat. No. 4,177,171 discloses a low irritation shampoo composition comprising 5-20% by weight of a combination of an amphoteric / anionic surfactant complex together with 8-20% by weight of a C16-C18 fatty acid mono ester of sorbitan reacted with 60-80 moles of ethylene oxide.

GB1508929 describes shampoos with a very low eye irritation potential along with excellent foaming and cleansing characteristics based on combinations of an ampholytic 2-alkyl-substituted imidazoline surfactant, a non-ionic surfactant which is one of a certain group of polyoxyethylene-polyoxypropylene block copolymer and an anionic alcohol-ether sulfate surfactant.

CA1077849 relates to high lathering detergent compositions having excellent foam stability and low ocular irritation comprising a betaine surfactant, an anionic surfactant and a polyoxyethylene derivative of a hydrophobic base as a non-ionic surfactant in a weight ratio of about 1:1:3.

CA1080625 describes conditioning and cleansing shampoo compositions which are non-irritating to the eyes and comprise a 1:1 molar ratio complex of an amphoteric surfactant and an anionic surfactant; a non-ionic surfactant; and a cationic quaternary-nitrogen based hydroxycellulose ether polymer.

EP0160269 describes a mild shampoo formulation containing an anionic surfactant, an imidazolinium or sulphosuccinate derivative, an amine oxide derivative and an ethoxylated dihydric or polyhydric alcohol derivative. The combination of an amine oxide derivative and a dihydric or polyhydric alcohol derivative is said to improve the mildness and increase the viscosity of the formulation.

These documents, and others, suggest the use of an ethoxylated non ionic polymer, for example an ethoxylated sorbitan ester, in order to increase the mildness of a shampoo composition. However a major drawback of using ethoxylated surfactants (whether non ionic or otherwise) is that they may contain 1,4-dioxane as an impurity and this has been identified as a carcinogen.

It is an aim of the present invention to provide a composition having low skin and ocular irritation and which comprises very low levels of ethoxylate-containing surfactants.

According to a first aspect of the present invention there is provided a low irritancy cleansing composition comprising:
(a) an anionic surfactant compound of formula (I):

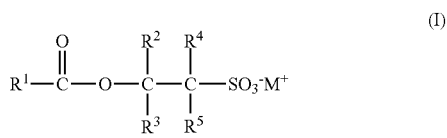

wherein $R^1$ represents a $C_{4-36}$ substituted or unsubstituted hydrocarbyl group;
each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen and $M^+$ represents a cation; and
(b) an amphoteric surfactant;
wherein the molar ratio of component (a) to component (b) is from 0.25:1 to 4:1 and wherein the composition comprises less than 3 wt % polyethoxylated non-ionic species.

Component (a) comprises an anionic surfactant compound of formula (I):

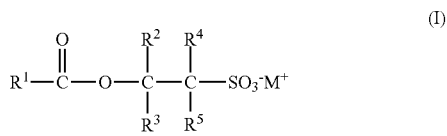

Preferably $R^1$ is selected from a substituted or unsubstituted alkyl, alkenyl, aryl or alkylaryl group. More preferably $R^1$ is selected from a substituted or unsubstituted alkyl or alkenyl group. Most preferably $R^1$ is an unsubstituted alkyl or alkenyl group, especially an unsubstituted alkyl group.

Preferably $R^1$ represents a $C_{5-30}$ alkyl group, preferably a $C_{7-24}$ alkyl group, more preferably a $C_{7-21}$ alkyl group, most preferably a $C_{7-17}$ alkyl group.

Preferably $R^2$ represents a $C_{1-4}$ alkyl group, suitably a $C_{1-4}$ alkyl group in which a propyl or butyl group, when present, is straight-chained. Preferably $R^2$ represents an n-propyl, ethyl or, most preferably, a methyl group.

Preferably $R^3$ represents a hydrogen atom.

Preferably one of $R^4$ and $R^5$ represents a hydrogen atom and the other represents a hydrogen atom or a $C_{1-4}$ alkyl group. Preferably one of $R^4$ and $R^5$ represents a hydrogen atom or a $C_{1-4}$ alkyl group in which a propyl or butyl group is straight-chain. Preferably one of $R^4$ and $R^5$ represents an n-propyl, ethyl or methyl group or, most preferably, a hydrogen atom. Most preferably both $R^4$ and $R^5$ represent hydrogen atoms.

In some embodiments the present invention may include a mixture of more than one compound of formula (I). For example an isomeric mixture of compounds of formula (I) may be present. Such a mixture may include, for example a compound in which $R^2$ is alkyl (suitably methyl) and $R^3$, $R^4$ and $R^5$ are all hydrogen and a compound in which $R^5$ is is alkyl (suitably methyl) and $R^2$, $R^3$ and $R^4$ are all hydrogen.

Preferably $M^+$ represents an optionally substituted ammonium cation or, most preferably, a metal cation. Suitable ammonium cations include $NH_4^+$ and the ammonium cation of triethanolamine. Suitable metal cations include alkali metal cations, for example sodium, lithium and potassium cations, and alkaline earth metal cations, for example calcium and magnesium cations. Preferably $M^+$ represents a potassium cation, or, especially, a sodium cation.

$R^1$ may be an alkyl group or an alkenyl group. Preferably $R^1$ is an alkyl group. In some embodiments the component surfactant of the present invention may comprise a mixture of fatty acids to form a mixture of compounds of formula (I) in which $R^1$ may be different.

$R^1$ is preferably the residue of a fatty acid. Fatty acids obtained from natural oils often include mixtures of fatty acids. For example the fatty acid obtained from coconut oil contains a mixture of fatty acids including $C_{12}$ lauric acid, $C_{14}$ myristic acid, $C_{16}$ palmitic acid, $C_8$ caprylic acid, and $C_{18}$ stearic and oleic.

$R^1$ may include the residue of one or more naturally occurring fatty acids and/or of one or more synthetic fatty acids. In some preferred embodiments $R^1$ consists essentially of the residue of a single fatty acid.

Examples of carboxylic acids from which $R^1$ may be derived include coco acid, butyric acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentanoic acid, behinic acid, erucic acid, docosahexanoic lignoceric acid, naturally occurring fatty acids such as those obtained from coconut oil, tallow, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof. Most preferably $R^1$ comprises the residue of lauric acid, that is a saturated fatty acid having 12 carbon atoms or the residue of mixed fatty acids derived from coconut oil.

The compound of formula (I) may be prepared by any of the methods disclosed in the prior art, for example see the methods described in WO94/09763 and WO2005/075623.

In especially preferred embodiments, $R^3$, $R^4$ and $R^5$ are all hydrogen and $R^2$ is ethyl or, most preferably, methyl.

In such preferred embodiments the composition of the present invention preferably comprises the reaction product of sodium methyl isethionate and a fatty acid, that is a compound of formula (II):

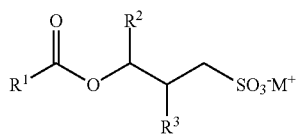

(II)

in which one of $R^2$ and $R^3$ is methyl and the other is hydrogen. Mixtures of these isomers may be present.

In some embodiments the composition of the present invention comprises one or more of sodium lauroyl methyl isethionate, sodium cocoyl methyl isethionate and sodium oleoyl methyl isethionate.

Most preferably the composition of the present invention comprises sodium lauroyl methyl isethionate and/or sodium cocoyl methyl isethionate. Sodium lauroyl methyl isethionate is especially preferred.

Component (b) comprises an amphoteric surfactant.

By amphoteric surfactant we mean to include any surfactants having the ability to exhibit both positive and negative sites. The surfactant component (b) may be selected from surfactants referred to as betaines, including sultaines (sulphobetaines), or other zwitterionic or amphoteric surfactants, for example those based on fatty nitrogen derivates.

Suitable surfactants for use as component (b) may be selected from betaines, for example alkyl betaines, alkylamidopropyl betaines, alkylamidopropyl hydroxy sultaines, alkylampho acetates, alkylamphodiacetates, alkylamphopropionates, alkylamphodipropionates, alkyliminodipropionates and alkyliminodiacetates.

Surfactants suitable for use as component (b) in the compositions of the present invention may include those which have an alkyl or alkenyl group of 7 to 22 carbon atoms and comply with an overall structural formula:

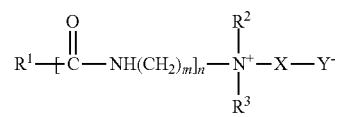

where $R^1$ is alkyl or alkenyl of 7 to 22 carbon atoms; $R^2$ and $R^3$ are each independently alkyl, hydroxyalkyl or carboxyalkyl of 1 to 6 carbon atoms; m is 2 to 4; n is 0 or 1; X is alkylene of 1 to 6 carbon atoms optionally substituted with hydroxyl; and Y is $—CO_2$ or $—SO_3$.

Surfactant component (b) may include simple betaines of formula:

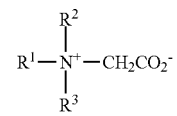

and amido betaines of formula:

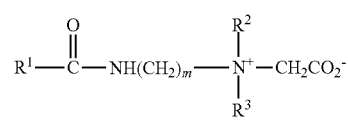

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters, of the groups $R^1$ has 10 to 14 carbon atoms. $R^2$ and $R^3$ are preferably methyl.

Surfactant component (b) may include sultaines (or sulphobetaines) of formula:

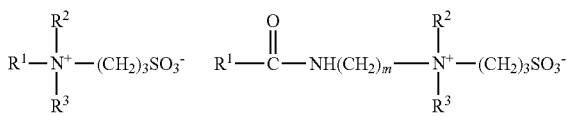

where m is 2 or 3, or variants of these in which
$—(CH_2)_3SO_3^-$ is replaced by

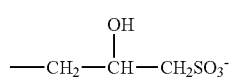

where $R^1$, $R^2$ and $R^3$ in these formulae are as defined previously.

Amphoteric or zwitterionic surfactants may include amphoacetates and diamphoacetates. Amphoacetates generally conform to the following formula:

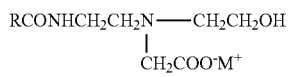

Diamphoacetates generally conform to the following formula:

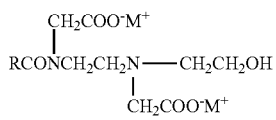

where R is an aliphatic group of 8 to 22 carbon atoms and M is a cation such as sodium, potassium, ammonium, or substituted ammonium.

Suitable acetate-based amphoteric surfactants include lauroamphoacetate; alkyl amphoacetate; cocoampho(di)acetate; cocoamphoacetate; disodium cocoamphodiacetate; sodium cocoamphoacetate; disodium cocoamphodiacetate; disodium capryloamphodiacete; disodium lauroamphoacetate; sodium lauroamphoacetate and disodium wheatgermamphodiacetate.

Suitable betaine surfactants include alkylamido betaine; alkyl betaine, $C_{12/14}$ alkyldimethyl betaine; cocoamidopropylbetaine; tallow bis(hydroxyethyl)betaine; hexadecyldimethylbetaine; cocodimethylbetaine; alkyl amido propyl sulfo betaine; alkyl dimethyl amine betaine; coco amido propyl dimethyl betaine; alkyl amido propyl dimethyl amine betaine; cocamidopropyl betaine; lauryl betaine; laurylamidopropl betaine, coco amido betaine, lauryl amido betaine, alkyl amino betaine; alkyl amido betaine; coco betaine; lauryl betaine; diemethicone propyl PG-betaine; oleyl betaine; N-alkyldimethyl betaine; coco biguamide derivative, $C_8$ amido betaine; $C_{12}$ amido betaine; lauryl dimethyl betaine; alkylamide propyl betaine; amido betaine; alkyl betaine; cetyl betaine; oleamidopropyl betaine; isostearamidopropyl betaine; lauramidopropyl betaine; 2-alkyl-N-carboxymethyl-N-hydroxyethyl imidazolinium betaine; 2-alkyl-N-carboxyethyl-N-hydroxyethyl imidazolinium betaine; 2-alkyl-N-sodium carboxymethyl-N-carboxymethyl oxyethyl imidazolinium betaine; N-alkyl acid amidopropyl-N,N-dimethyl-N-(3-sulfopropyl)-ammonium-betaine; N-alkyl-N,N-dimethyl-N-(3-sulfopropyl)-ammonium-betaine; cocodimethyl betaine; apricotamidopropyl betaine; isostearamidopropyl betaine; myristamidopropyl betaine; palmitamidopropyl betaine; cocamidopropyl hydroxy sultaine; undecylenamidopropyl betaine; cocoamidosulfobetaine; alkyl amido betaine; $C_{12/18}$ alkyl amido propyl dimethyl amine betaine; lauryldimethyl betaine; ricinol amidobetaine; tallow aminobetaine.

Suitable glycinate-based amphoteric surfactants include cocoamphocarboxyglycinate; tallowamphocarboxygycinate; capryloamphocarboxyglycinate, oleoamphocarboxyglycinate, bis-2-hydroxyethyl tallow glycinate; lauryl amphoglycinate; tallow polyamphoglycinate; coco amphoglycinate; oleic polyamphoglycinate; N—$C_{10/12}$ fatty acid amidoethyl-N-(2-hydroxyethyl)-glycinate; N—$C_{12/18}$-fatty acid amidoethyl-N-(2-hydroxyethyl)glycinate; dihydroxyethyl tallow glycinate.

Preferred acetate-based amphoteric surfactants for use as component (b) include sodium lauroamphoacetate, disodium lauroamphoacetate and mixtures thereof.

Preferred betaine surfactants for use as component (b) include cocoamidopropyl betaine.

Preferred sultaine surfactants for use as component (b) include cocoamidopropylhydroxy sultaine.

In especially preferred embodiments the cleansing composition of the present invention comprises:
    an anionic surfactant selected from sodium lauryl methyl isethionate, sodium cocoyl methyl isethionate, sodium oleoyl methyl isethionate and mixtures thereof; and
    an amphoteric surfactant selected from sodium lauroamphoacetate, disodium lauroamphotacetate, cocoamidopropyl betaine, cocoamidopropylhydroxy sultaine and mixtures thereof.

Component (a) is preferably present in the cleansing composition of the present invention in an amount of at least 0.5 wt %, preferably at least 1 wt %, for example at least 1.5 wt %, suitably at least 2 wt % or at least 2.5 wt %. Component (a) may be present in an amount of up to 50 wt %, preferably up to 40 wt %, suitably up to 30 wt %, preferably up to 20 wt %, more preferably up to 10 wt %, for example up to 7.5 wt % or up to 5 wt %.

Component (b) is preferably present in the cleansing composition of the present invention in an amount of at least 0.5 wt %, preferably at least 1 wt %, for example at least 1.5 wt %, suitably at least 2 wt % or at least 2.5 wt %. Component (b) may be present in an amount of up to 50 wt %, preferably up to 40 wt %, suitably up to 30 wt %, preferably up to 20 wt %, more preferably up to 10 wt %, for example up to 7.5 wt % or up to 5 wt %.

The composition of the present invention may comprise further surfactant components in addition to components (a) and (b). Such surfactants may be selected from anionic surfactants, cationic surfactants, amphoteric surfactants, non-ionic surfactants and mixtures thereof. The selection of suitable further surfactants for use in the composition of the present invention is within the competence of the person skilled in the art. For example cationic quaternary ammonium compounds are useful as conditioning agents.

The composition of the present invention comprises less than 3 wt % polyethoxylated non-ionic species. By polyethoxylated non-ionic species we mean to refer to a compound which has been prepared by reaction with ethylene oxide and includes at least two residues $CH_2CH_2O$. Polyethoxylated non-ionic species include surfactant compounds and other ethoxylated materials for example polymers, such as ethylene oxide-propylene oxide block copolymers. Non-ionic surfactant compounds suitably comprise a hydrophobic group and two or more ethylene oxide residues. Such compounds are suitably formed by reacting aliphatic alcohols, acids, amides or alkyl phenyl with ethylene oxide.

Preferably the composition of the present invention comprises less than 2.5 wt % polyethoxylated non-ionic species, preferably less than 2 wt %, more preferably less than 1.5 wt %, preferably less than 1 wt %, suitably less than 0.75 wt %, more preferably less than 0.5 wt %, preferably less than 0.25 wt %, preferably less than 0.1 wt %, suitably less than 0.05 wt %, for example less than 0.01 wt %, preferably less than 0.005 wt % and most preferably less than 0.001 wt %.

Thus the cleansing composition of the present invention is preferably substantially free of polyethoxylated non-ionic species. Most preferably the composition of the present invention is completely free of polyethoxylated non-ionic species.

Preferably the cleansing composition comprises less than 3 wt % ethoxylated non-ionic species comprising one or more ethylene oxide residues, preferably less than 1 wt %, more preferably less than 0.5 wt %, preferably less than 0.1 wt %, more preferably less than 0.05 wt %, preferably less 0.01 wt %, preferably less than 0.005 wt % and most preferably less than 0.001 wt %.

As the skilled person will appreciate other classes of surfactant, for example cationic surfactants, amphoteric surfactants and anionic surfactants may also be ethoxylated. Surfactants of this type may also include low levels of 1,4-dioxanes as an impurity. It is therefore preferred that the composition of the present invention comprises less than 3 wt % in total of ethoxylated surfactant compounds of any type, preferably less than 2 wt %, more preferably less than 1.5 wt %, suitably less than 1 wt %, preferably less than 0.75 wt %, more preferably less than 0.50 wt %, suitably less than 0.25 wt %, preferably less than 0.1 wt %, more preferably less than 0.5 wt %, suitably less than 0.25 wt %, preferably less than 0.1 wt % more preferably less than 0.01 wt % and most preferably less than 0.001 wt %.

Preferably the composition of the present invention comprises less than 1000 ppm 1,4-dioxanes, preferably less than 500 ppm, more preferably less 250 ppm, suitably less than 125 ppm, preferably less than 75 ppm, more preferably less than 50 ppm, preferably less than 30 ppm and most preferably less than 20 ppm. In especially preferred embodiments the composition of the present invention comprises less than 10 ppm 1,4-dioxanes, preferably less than 8 ppm, more preferably less than 5 ppm, suitably less than 2.5 ppm and most preferably less than 1 ppm.

It is also desirable that the composition of the present invention does not contain alkoxylated non-ionic surfactant compounds. Thus in preferred embodiments the composition of the present invention comprises less than 3 wt % alkoxylated non-ionic surfactant compounds preferably less than 2 wt %, more preferably less than 1 wt %, preferably less than 0.5 wt %, suitably less than 0.25 wt %, preferably less than 0.1 wt %, more preferably less than 0.05 wt %, suitably less than 0.01 wt %, and most preferably less than 0.001 wt %.

In especially preferred embodiments the composition of the present invention is substantially free of alkoxylated non-ionic surfactant compounds.

It is advantageous that the present invention does not comprise significant amounts of alkoxylated surfactant compounds of any type, especially polyalkoxylated surfactant compounds, including non-ionic, cationic, amphoteric or anionic surfactants. Thus in preferred embodiments the composition of the present invention comprises less than 3 wt % polyalkoxylated surfactant compounds, preferably less than 2 wt %, more preferably less than 1 wt %, suitably less than 0.75 wt %, preferably less than 0.50 wt %, more preferably less than 0.25 wt %, preferably less than 0.1 wt %, more preferably less than 0.01 wt % and most preferably less than 0.001 wt %. Preferably the composition of the present invention comprises less than 3 wt % alkoxylated surfactant compounds, preferably less than 1 wt %, suitably less than 0.1 wt %, more preferably less than 0.01 wt % and most preferably less than 0.001 wt %.

In preferred embodiments the cleansing composition of the present invention is substantially free of alkoxylated surfactant compounds of any type.

The composition of the present invention may comprise further surfactant components in addition to components (a) and (b). Such surfactants may be selected from anionic surfactants, cationic surfactants, amphoteric surfactants, non-ionic surfactants and mixtures thereof. The selection of suitable further surfactants for use in the composition of the present invention is within the competence of the person skilled in the art. For example cationic surfactants comprising quaternary nitrogen salts may be used as conditioning agents.

In preferred embodiments components (a) and (b) together comprise at least 70 wt % of all surfactants present in the composition, preferably at least 75 wt %, more preferably at least 80 wt %, suitably at least 85 wt %, more preferably at least 90 wt %, preferably at least 95 wt % and most preferably at least 98 wt %.

The molar ratio of component (a) to component (b) is between 0.25 and 4:1. Preferably it is between 0.4:1 and 3:1, more preferably between 0.5:1 and 2:1, preferably between 0.6:1 and 1.7:1, more preferably between 0.8:1 and 1.5:1, more preferably between 0.9:1 and 1.2:1.

The skilled person will appreciate that commercially available sources of surfactants often include significant levels of impurities. The levels of impurity present in commercial surfactants may be up to 25% or even 30% by weight and these impurities usually contain unreacted starting materials and/or byproducts.

For the avoidance of doubt, unless otherwise stated, any definitions of amounts of surfactant stated herein and molar and weight ratios thereof refer to the actual amount of active surfactant compound present in the composition.

As mentioned above, each of components (a) and (b) may comprise a mixture of the specified surfactant and any amount mentioned in this specification refers to the total amount of each such surfactant type present in the composition. As will be readily understood by the skilled person, commercial sources of surfactant often comprise mixtures of active surfactant compounds (as well as impurities), for example different isomers, especially if they have been prepared from natural sources, for example fatty acid mixtures found in nature.

The composition of the present invention may comprise one or more further components selected from antibacterial agents, foam boosters, pearlescers, perfumes, dyes, colouring agents, preservatives, thickeners, proteins, polymers such as silicone polymers, phosphate esters, sunscreens, antidandruff agents, buffering agents, moisturisers such as fatty acid alkanolamides, silicone derivatives, cationic polymers, propylene glycol, glycerine, viscosity controlling agents such as methyl cellulose, and other additives which usually used for cleansers.

Suitable conditioning agents include quaternary ammonium compounds of formula

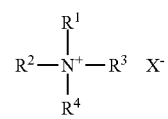

wherein each of $R^1$, $R^2$, $R^3$ and $R^4$ is an alkyl or alkenyl group and X is chloride, bromide or methyl sulfate. At least one of $R^1$, $R^2$, $R^3$ and $R^4$ is a $C_6$ to $C_{24}$ alkyl or alkenyl group and the others are $C_1$ to $C_4$ alkyl, for example methyl. In some embodiments two, three or four of the groups $R^1$, $R^2$, $R^3$ and $R^4$ may be $C_6$ to $C_{24}$ alkyl or alkenyl.

Suitable conditioning agents for use herein include those designated as polyquaterniums on the INCI list, for example polyquaternium-10 and polyquaternium-7; as well as guar hydroxypropyl ammonium chloride and similar cationic polymers.

Suitable preservatives include dimethyl dimethylolhydantoin (DMDMH), DMDMH/iodopropynyl-butyl carbamate (Glydant Plus, a registered trademark of Lonza Inc.), benzyl alcohol, methyl paraben, propyl paraben and imidazolidinyl urea. Of course there are many additional preservatives that will function effectively in cleansings.

Suitably the cleansing composition of the present invention has a pH of from 4 to 8, preferably from 4.5 to 7, for example from 4.5 to 6. The pH can be adjusted, as needed, with either a base, for example sodium hydroxide or sodium carbonate or an acid for example citric acid, succinic acid, or phosphoric acid.

The present invention is preferably an aqueous composition. In some embodiments the composition may comprise one or more further solvents in addition to water. Such suitable co-solvents may include polar compounds for example alcohols, glycols and the like.

However in preferred embodiments water is the major solvent present in the composition of the present invention and suitably comprises at least 80 wt % of all solvents present, preferably at least 90 wt %, more preferably at 95 wt %.

The present invention provides a low irritancy cleansing composition. Preferably the composition of the present invention is very low irritating to both the skin and the eyes.

The cleansing composition may be used for any purpose in which low irritancy to the skin and/or eyes is desirable. For example the composition may be used as a facial wash or a product for people with sensitive skin. Most preferably the composition of the present invention is a baby care product, for example a baby bath product or a baby shampoo.

Suitably the cleansing composition of the present invention is sufficiently non-irritating to enable it to be used as a baby shampoo.

In particular it is desired that the composition of the present invention exhibits very low ocular irritation.

Ocular irritation can be measured by any suitable method and such methods will be known to the person skilled in the art. A standard method known since 1944 is the Draize Eye Irritancy Test. This is a long established test which involves delivery of a material into the conjunctival sac of one eye of a rabbit. However this test is now used less often as it is often considered cruel and alternative in vitro tests have been developed. One suitable method is the "EpiOcular"® of MatTek. This corneal model consists of normal, human-derived epidermal keatinocytes which have been cultured to form a stratified, squamous epithelium similar to that found in the cornea. The epidermal cells, which are cultured on specially prepared cell culture inserts using serum free medium, differentiate to form a multilayered structure which closely parallels the corneal epithelium. The system is said to provide a predictive, morphologically relevant in vitro means to assess ocular irritancy. The results from the EpiOculuar® test allow a composition to be classified as highly irritating, irritating, mildly irritating or minimally or non-irritating. Such a test is used in the examples.

Suitably the low irritancy cleansing formulation of the present invention would be classified as mildly irritating or minimally or non-irritating. Preferably it would be classified as non-irritating or minimally irritating.

Details of the EpiOcular® test can be found in the paper entitled "Evaluation of the EpiOcular™ Tissue Model as an Alternative to the Draize Eye Irritation Test"; M. Stern, M. Klausner, R. Alvarado, K. Renskers, M. Dickens; *Toxicology in Vitro*, Volume 12, Issue 4, August 1998, Pages 455-461.

As mentioned above there are a number of eye irritancy tests available. Many of these tests allow the results to be correlated to provide an equivalent score on the Draize test. In order to allow a correlation to be made it is often necessary to carefully select appropriate conditions, especially concentration. However the performance of such a test would be well with the competence of the skilled person.

The composition of the present invention would preferably be such that when testing using in vitro tests of this type it would provide a score equivalent to mild or non-irritating on the Draize Test.

Preferably the cleansing composition of the present invention has low skin irritancy. Skin irritancy may be measured by any suitable means. In one common method a composition is applied to the skin for 14 consecutive days and the irritation evaluated in what is referred to as a 14-Day Cumulative Irritation Test. Such a test is described in the examples.

The low irritancy cleansing composition of the present invention is very mild and can thus be used as a baby shampoo, baby bath, mild skin cleanser, facial skin cleanser, sensitive skin cleanser and the like. The composition is particularly advantageous as it contains very much lower levels of ethoxylated non-ionic surfactants than have been previously used and thus any 1,4-dioxane will be present in a lower amount, preferably in amount which is undetectable.

Because the composition of the present invention preferably does not comprise a non-ionic polyethoxylated species it has fewer components than cleansing compositions of the prior art. As such it is cheaper and easier to prepare and has an improved environmental profile.

The low irritancy cleansing composition of the present invention could also be used in animal care applications, for example as a pet shampoo.

According to a second aspect of the present invention there is provided a concentrated surfactant composition which upon dilution forms a low irritancy cleansing composition of the first aspect of the present invention.

Preferred features of the second aspect are as defined in relation to the first aspect.

The invention will now be further described by reference to the following non-limiting examples.

EXAMPLE SET 1

Compositions were prepared comprising the following active ingredients:
 1a—0.5 wt % of sodium cocoyl methyl isethionate (SCMI)
 1b—0.5 wt % of sodium lauryl amphoacetate (SLAA)
 1c—0.5 wt % of a 1:1 molar ratio of SCMI:SLAA
 1d—deionised water.

These compositions were then tested to evaluate the human cumulative dermal irritation potential using the following 14-Day Cumulative Irritation Test:

Twenty-two subjects (1 male and 21 females ranging in age from 28 to 70 years), were empanelled for the test. The subjects chosen were dependable, able to read and understand instructions, and did not exhibit any physical or dermatological condition that would have precluded application of the test compositions.

Test Procedure

Approximately 0.1-0.15 g of each test article was placed onto a Parke-Davis Readi-Bandage® occlusive patch that measured 2 cm×2 cm. The patch was then applied to the back of each subject between the scapulae and waist, adjacent to the spinal mid-line. These patches were secured with hypoallergenic tape (Scanpor [Allerderm]), as needed. The designed patch test site measured approximately 2.54 cm×2.54 cm (1"×1"), on the infrascapular area of the back, to the right and lest of the midline. Patches applied on Saturday were left in place until Monday, when freshly prepared patches were applied.

Each day following application, the patches were removed, the sites evaluated and identical patches reapplied to the same test sites. All evaluations were made by the evaluator using the following 6-point scale:
Irritating Scoring Scale
  0=No reaction
  0.5=Barely perceptible (minimal, faint, uniform or spotty erythema, alpha-numeric value=+)
  1=Mild (pink, uniform erythema covering most of the contact site)
  2=Moderate (pink-red erythema visibly uniform in entire contact site)
  3=Marked (bright red erythema with/without petechiae or papules)
  4=Severe (deep red erythema with/without visculation or weeping)

All other observed dermal sequelae (eg, edema, dryness, hypo- or hyper-pigmentation) were appropriately recorded on the data sheet and described as mild, moderate or severe.

Based on 20 subjects completing the study, the highest total cumulative irritation score that could be obtained was 1120 (20 subjects×14 days×"4" [highest obtainable irritation score for any of the test articles]). The highest possible mean cumulative irritation score that could be obtained was 56 (1120÷20 subjects).

The results of the study were as follows:
Composition 1a: 23
Composition 1b: 16
Composition 1c: 10 (of the invention)
Composition 1d: 6

The results of the study show that the combination of an equimolar amount of SCMI and SLAA showed reduced irritation compared to the use of either component alone. This reduction in irritancy was achieved without the addition of an ethoxylated species.

EXAMPLE SET 2

The compositions prepared were as follows:

|   |   | Example 2a | Example 2b | Example 2c (of the invention) | Example 2d (of the invention) |
|---|---|---|---|---|---|
| A | ISELUX 20% Active SLMI Aq. Soln | 50 wt % |  | 25 wt % | 25 wt % |
| B-1 | Cocamidopropyl Betaine 30% Active |  |  |  | 16.67 wt % |
| B-2 | Sodium Lauroamphoacetate 30% Active |  | 33.33 wt % | 16.67 wt % |  |
|  | NATRLQUEST E-30-trisodium EDDS chelant, 40% Active | 0.9 wt % | 0.9 wt % | 0.9 wt % | 0.9 wt % |
|  | Deionised Water | 49.1 wt % | 65.77 wt % | 57.43 wt % | 57.43 wt % |
|  | 50% Citric Acid (to achieve pH 6.0) | QS | QS | QS | QS |
|  | % Active SLMI—A | 10 wt % |  | 5 wt % | 5 wt % |
|  | % Active Betaine—B-1 or Amphoacetate B-2 |  | 10 wt % | 5 wt % | 5 wt % |
|  | Molar Ratio A/B | N/A | N/A | 1.0/0.97 | 1.0/1.05 |

SLMI is sodium lauroyl methyl isethioniate.

The compositions were tested, as 10 wt % dilutions in water, using the EPIOCULAR in vitro test described above. The results were as follows:

Calculated Draize Score

| Example 2a | Example 2b | Example 2c (of the invention) | Example 2d (of the invention) |
|---|---|---|---|
| 10.8 | 3.2 | 3.0 | 2.7 |

The correlation between calculated scores and irritation category is shown below

| Calculated Draize Score | Irritation Category |
|---|---|
| 0-15 | Non Irritating (0 score)/Minimal |
| 15.1-25 | Mild |
| 25.1-50 | Moderate |
| 50.1-110 | Severe/Extreme |

The irritation studies show that all of the formulas were minimally irritating, but that the combinations of the invention were less irritating than the SLMI alone.

ISELUX, NATRLQUEST and EPIOCULAR are registered trade marks.

The invention claimed is:
1. A low irritancy cleansing composition comprising:
  (a) 0.5 wt % to 5 wt % of sodium lauroyl methyl isethionate; and
  (b) 0.5 wt % to 7.5 wt % an amphoteric betaine surfactant or amphoteric sultaine surfactant;
  wherein the molar ratio of component (a) to component (b) is from 0.5:1 to 2:1 and wherein the composition comprises less than 3 wt % polyethoxylated non-ionic species.
2. The composition according to claim 1 wherein the ratio of component (a) to component (b) is from 0.8:1 to 1.3:1.

3. The composition according to claim 1 which comprises less than 0.001 wt % polyethoxylated non-ionic species and is preferably free of polyethoxylated non-ionic species.

4. The composition according to claim 1 which comprises less than 0.1 wt % ethoxylated non-ionic species.

5. The composition according to claim 1 which comprises less than 0.1 wt % ethoxylated surfactant compounds of any type.

6. The composition according to claim 1 which comprises less than 0.1 wt % alkoxylated non-ionic surfactant compounds.

7. The composition according to claim 1 which comprises less than 0.1 wt % aikoxylated surfactant compounds of any type.

8. The composition according to claim 1 which is classified as non-irritating, minimally irritating or mildly irritating on the EpiOcular® test.

9. The composition according to claim 1 which exhibits mild or no skin irritancy on a 14-day cumulative irritation test.

10. The composition according to claim 1 which is selected from the group consisting of a baby shampoo, a baby bath, a mild skin cleanser, a facial cleanser and a sensitive skin cleanser.

11. The composition according to claim 1, wherein component (b) is selected from the group consisting of sulphobetaine, cocoamidopropyl betaine, cocoamidopropylhydroxy sultaine, sodium lauroamphoacelate disodium lauroamphoacetate and mixtures thereof.

\* \* \* \* \*